June 15, 1943. J. S. LECKIE Plant Pat. 592
PEACH
Filed Sept. 18, 1941
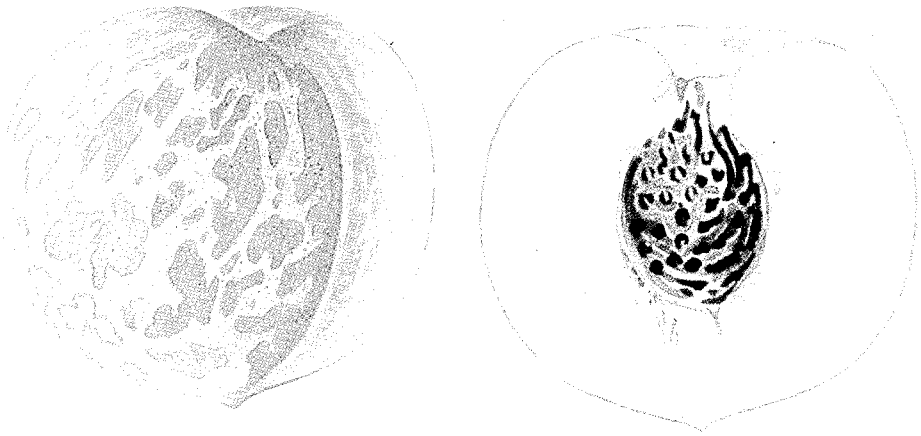
INVENTOR
John Stuart Leckie
By Eugene E. Stevens
Atty.

Patented June 15, 1943

Plant Pat. 592

UNITED STATES PATENT OFFICE

592

PEACH

John Stuart Leckie, Osoyoos, British Columbia, Canada

Application September 18, 1941, Serial No. 411,411

1 Claim. (Cl. 47—62)

This invention relates to a new peach, the novel characteristics of which are its early date of ripening, and its improved appearance with regard to colour and shape.

The sport was discovered on a Rochester peach tree, wood buds from this sport were grafted on to other peach trees and they took. These buds reproduced duplicates of the original branch, each having fruit buds which in the following spring developed into peaches. These peaches ripened approximately from 14 to 20 days before the Rochester peach.

The following is a description of this novel peach:

*Size.*—Equal to or larger than a Rochester peach.

*Colour.*—It has a much brighter yellow or gold colour than the Rochester and is overlaid with a very high red blush, whereas the Rochester has a dull yellow and red combination.

*Shape.*—Resembles closely the shape of the J. H. Hale peach. It is more round than the Rochester and has a pronounced point on the bottom.

*Flesh.*—Firm, yellow and very sweet, semi-free to free-stone.

*Skin.*—Smooth with much less fuzz than that of a Rochester.

*Date of ripening.*—Between 15 and 20 days before the Rochester.

This peach is more attractive in colour and shape than the Rochester peach.

The estimate of from 15 to 20 days earlier than the Rochester as the ripening date of this peach is as close as possible owing to different climatic conditions. In one test, these peaches were ready for picking for shipment on July 15, while the Rochesters on the same tree were not ready until August 2, a difference of 19 days.

The features which are claimed to distinguish this new variety from all other varieties of peaches are as follows:

First: The bright yellow and gold colour which is overlaid with a very high red blush.

Second: The smoothness of the skin and the reduced amount of fuzz.

Third: The earlier ripening date, between 15 and 20 days earlier than the Rochester peaches.

I claim:

The variety of peach herein described, characterized particularly by its early ripening date of between 15 and 20 days earlier than a Rochester peach, its bright yellow and gold colour overlaid with a very high red blush, and its smooth skin with comparatively little fuzz.

JOHN STUART LECKIE.